United States Patent [19]

Masuhara et al.

[11] 4,362,842
[45] Dec. 7, 1982

[54] COMPOSITE FILLER AND DENTAL COMPOSITION CONTAINING THE SAME

[75] Inventors: Eiichi Masuhara, Tokyo; Nobuo Nakabayashi, Matsudo; Katsuhisa Nagata, Yachiyo; Morio Takeyama, Tokyo, all of Japan

[73] Assignee: Mitsui Petrochemical Industries, Ltd., Tokyo, Japan

[21] Appl. No.: 171,032

[22] Filed: Jul. 22, 1980

[30] Foreign Application Priority Data

Jul. 27, 1979 [JP] Japan ................................. 54/94897

[51] Int. Cl.$^3$ ...................... A61K 6/08; C08F 291/06; C08K 3/36
[52] U.S. Cl. ..................................... 524/854; 523/116
[58] Field of Search ............... 260/42.15, 42.53, 42.14, 260/42.52; 523/116; 524/854

[56] References Cited

U.S. PATENT DOCUMENTS

| | | | |
|---|---|---|---|
| 3,821,158 | 6/1974 | Westermann et al. | 260/42.53 |
| 3,833,682 | 9/1974 | Dickie et al. | 525/306 |
| 3,835,090 | 9/1974 | Gander et al. | 260/42.15 |
| 3,907,656 | 9/1975 | Souza | 260/42.52 |
| 3,988,393 | 10/1976 | Gallagher | 260/29.7 UA |
| 4,043,988 | 8/1977 | Cooke et al. | 260/40 R |
| 4,082,895 | 4/1978 | Backderf et al. | 260/29.6 PM |
| 4,200,980 | 5/1980 | Johnston | 433/8 |
| 4,221,698 | 9/1980 | Lee et al. | 260/42.53 |

FOREIGN PATENT DOCUMENTS

| | | |
|---|---|---|
| 44-7541 | 4/1969 | Japan . |
| 48-90332 | 11/1973 | Japan . |
| 53-35978 | 9/1978 | Japan . |
| 1312816 | 4/1973 | United Kingdom . |
| 1369570 | 10/1974 | United Kingdom . |
| 1395379 | 3/1975 | United Kingdom . |
| 1463876 | 2/1977 | United Kingdom . |

OTHER PUBLICATIONS

Derwent Abst. 40150 V/29 (DT 2163660), Ford-Werke, (7-5-73).
Derwent Abst. 29409 X/16 (J76008975), Yamauchmi, M., (3-23-76).
Derwent Abst. 85058 V/49, (J49057054), Mochida, (6-3-74).

Primary Examiner—Paul Lieberman
Assistant Examiner—Herbert J. Lilling
Attorney, Agent, or Firm—Cushman, Darby & Cushman

[57] ABSTRACT

A composite filler obtained by precuring the acrylate or methacrylate of a polyhydric alcohol having at least three ethylenically unsaturated groups in the molecule thereof by using a free-radical initiator in the presence of an inorganic filler, followed by grinding the resultant prepolymer is described. This composite filler remarkably improves the stiffness and hardness of organic resins and rubbers, and prevents a decrease in the impact strength and bending strength of organic resins and rubbers when the composite fillers are compounded into the organic resins and rubbers. Furthermore, a dental composition obtained from the polymerization of a vinyl compound in the presence of the above-mentioned composite filler is described. This dental composition has excellent properties, such as, high hardness, high strength, good adhesiveness, and is suitable for use as dental materials.

5 Claims, No Drawings

COMPOSITE FILLER AND DENTAL COMPOSITION CONTAINING THE SAME

The present invention relates to a composite filler suitable for compounding into various resins and rubbers. The present invention also relates to a dental composition containing the composite filler.

Recently, various inorganic fillers have been compounded into organic resins and rubbers to improve the properties of the organic resins and rubbers, for example, the compressive strength, the hardness, the chemical resistance, he flame retardance and the like. However, since the inorganic fillers generally have a poor affinity for organic resins and rubbers, the desired improvements in the properties of the organic resins and rubbers could not be obtained in the majority of cases. In order to obviate this problem, it has been proposed that composite fillers comprising inorganic fillers coated with organic compounds be compounded into organic resins and rubbers (see Japanese Patent Publication No. 53-35978/1978). However, satisfactory improvements could not be obtained by implementing this proposal.

The present inventors conducted detailed studies directed to the compounding of the inorganic fillers coated with organic compounds into organic resins and rubbers, and found that, since the organic compounds have no ethylenically unsaturated groups, or at most one or two ethylenically unsaturated groups, in the molecule, the resultant composite fillers have a poor reactivity due to the absence or small number of ethylenically unsaturated groups. In the case where one or two ethylenically unsaturated groups are present in the starting organic compounds, the unsaturated bonds are substantially consumed in the course of the coating step of the inorganic fillers. Furthermore, even in the case where the unsaturated bonds are present in the organic compounds and are consumed during the coating step to form cured bonds, the inorganic fillers are easy to move in the matrix of the cured products of the organic compounds, so that the inorganic fillers are not well dispersed in the composite fillers and, therefore, the stiffness, hardness and other properties of the organic resins and rubbers into which the composite fillers are compounded cannot be desirably improved.

An object of the present invention is to obviate the above-mentioned problem of the prior arts and to provide a composite filler which is capable of desirably improving the properties of organic resins and rubbers when the composite filler is compounded into resins and rubbers.

Another object of the present invention is to provide a dental composition suitable for use as a dental resin material and having improved compression strength, hardness and chemical resistance.

Other objects and advantages of the present invention will be apparent from the description set forth hereinbelow.

In accordance with the present invention, there is provided a composite filler obtained by precuring the acrylate or methacrylate of a polyhydric alcohol having at least three ethylenically unsaturated groups in the molecule thereof by using a free-radical initiator in the presence of an inorganic filler, followed by grinding the resultant prepolymer.

In accordance with the present invention, there is also provided a dental composition derived from the polymerization of a vinyl compound in the presence of a composite filler obtained by precuring the acrylate or methacrylate of a polyhydric alcohol having at least three ethylenically unsaturated groups in the molecule thereof by using a free-radical initiator in the presence of an inorganic filler, followed by grinding the resultant prepolymer.

Since the acrylates or methacrylates of polyhydric alcohols having at least three ethylenically unsaturated groups in the molecule thereof are employed as the organic compounds incorporated into the composite fillers, the resultant composite fillers of the present invention exhibit extremely high modification effects, compared to the above-mentioned conventional composite fillers, when the composite fillers are compounded into organic resins and rubbers. The action of the organic compounds employed in the present invention in the composite fillers is not clearly understood, but it is believed that, since the organic compounds employed in the present invention have three or more ethylenically unsaturated groups, all the ethylenically unsaturated groups in the organic compounds are not consumed during the coating step of the inorganic fillers, and therefore, the resultant composite fillers are very reactive and are chemically bonded to the organic resins and rubbers to be compounded. As a result, the decreases in the impact strength and bending strength of the organic resins and rubbers can be prevented. Furthermore, since the number of the ethylenically unsaturated groups in the organic compounds employed in the present invention is large, the number of the cured bonds in the resultant composite fillers becomes large. As a result, the inorganic fillers are difficult to move in the matrix of the cured products of the organic compounds and, therefore, the inorganic fillers are well dispersed in the composite fillers. Thus, the stiffness and hardness of the organic resins and rubbers are remarkably improved or modified by the compounding of the present composite fillers.

The composite fillers of the present invention can be prepared by precuring the acrylate or methacrylate of a polyhydric alcohol having at least three ethylenically unsaturated groups in the molecule thereof in the presence of an inorganic filler, followed by grinding the resultant prepolymer. The precuring is carried out in the presence of the inorganic filler by using a free-radical initiator, optionally by heating. The precuring is preferably terminated in such a manner that a portion of the ethylenically unsaturated groups in the acrylate or methacrylate remains. The remaining portion of the ethylenically unsaturated groups is preferably in such an amount that a relative ratio of the absorbance at 1635 cm$^{-1}$ (based on C=C bond) to the absorbance at 1730 cm$^{-1}$ (based on C=O bond) in infrared spectrum is 0.05 through 0.3. The prepolymer thus obtained is ground into powder having an appropriate shape and size. This grinding may also increase the reactivity of the prepolymer.

In the case where the inorganic fillers are coated with the organic compounds employed in the present invention, it is preferable that the inorganic fillers be previously mixed with the organic compounds. For instance, the premixing of the inorganic fillers and the organic compounds can be carried out by first mixing the inorganic fillers and the organic compounds in small amounts to form slightly viscous paste compositions, and then, adding the residual inorganic fillers, the residual organic compounds and the free-radical initiator to the paste composition, while the paste compositions are milled on a pair of rolls. Of course, a Banbury mixer, a ball mill and the like can be used in lieu of the rolls.

The mixing ratio of the organic compounds to the inorganic fillers is generally within the range of from 20:80 to 80:20, preferably 40:60 to 60:40, although the mixing ratio should be determined, depending upon, for example, the types, shapes and sizes of the inorganic fillers, the types of the organic compounds and the intended purposes and usages of the composite fillers. If the mixing ratio of the organic compounds to the inorganic fillers is less than 20:80, the stiffness and the hardness are not preferably improved. Contrary to this, if the mixing ratio is more than 80:20, uniform mixing cannot be obtained.

The inorganic fillers are coated with the above-mentioned organic compounds employed in the present invention by precuring the premixing products. The precuring is carried out by using, for example, a heating press at a temperature of 40° to 250° C., preferably 60° to 150° C., and under a pressure of 10 to 300 kg/cm²G, preferably 100 to 200 kg/cm²G, or under an inert atmosphere without pressure. As mentioned hereinabove, the precuring is preferably terminated by the stop of the heating, before all the ethylenically unsaturated groups in the organic compounds are consumed. The precuring time is generally within the range of from a few minutes to about one hour.

The grinding of the precured products can be carried out by using, for example, a ball mill until composite fillers having the desired shapes and sizes are obtained.

The inorganic fillers employed in the present invention include those which are conventionally recognized as inorganic fillers for organic resins and rubbers. Examples of such fillers are silane coated glass, alumina, quartz, silica, calcium carbonate, carbon black, clay, talc, diatomaceous earth, siliceous sand, pumice powder, slate flour, mica flake, asbestos, aluminum sulfate, barium sulfate, lithopone, calcium sulfate, molybdenum disulfide, graphite, glass fiber, fly ash, shirasu baloon, potassium titanate, carbon fiber and cryolite. The most preferable inorganic filler is silica, especially silica which is subjected to a surface treatment to impart a hydrophobic property to the silica. The shapes and the sizes of the inorganic fillers employed in the present invention are not critical and can be appropriately determined. The inorganic fillers can be employed alone or in any mixture thereof.

The organic compounds employed in the present invention include the acrylates or methacrylates of polyhydric alcohols having at least three ethylenically unsaturated groups in the molecules thereof. Examples of such organic compounds are polyvalent esters (i.e. triesters or more) of polyhydric alcohols (i.e. trialcohols or more), such as, glycerine, trimethylol ethane, trimethylol propane and pentaerythritol, with acrylic or methacrylic acid. Preferable examples of the organic compounds employed in the present invention are the triacrylate or trimethacrylate of glycerine, the triacrylate or trimethacrylate of trimethylol ethane, the triacrylate or trimethacrylate of trimethylol propane and the tetraacrylate or tetramethacrylate of pentaerythritol. The most preferable organic compound is the acrylate or methacrylate of trimethylol propane. These organic compounds can be employed alone or in any mixture thereof.

The free-radical initiators employed in the present invention may be any conventional free-radical initiators. Typical examples of such free-radical initiators are organic peroxides, such as dicumyl peroxide and benzoyl peroxide, and azobisisobutyronitrile. Although there is no critical concentration of the free-radical initiators in the premixing products, the free-radical initiators are generally used in an amount of from 0.01 to 3% weight, based on the weight of the mixture of the inorganic fillers and the organic compounds.

Since the inorganic fillers are well dispersed in the composite fillers of the present invention, the stiffness and the hardness of the organic resins and rubbers, into which the composite fillers of the present invention are compounded, are remarkably modified or improved when the composite fillers are compounded. Furthermore, since the composite fillers of the present invention are very reactive, and are chemically bonded to the organic resins and rubbers to be compounded, decreases in the impact strength and the bending strength of the organic resins and rubbers, into which the composite fillers are compounded, are effectively prevented. Thus, the performance and the effect of the composite fillers of the present invention are higher than those of the conventional composite fillers. Therefore, the composite fillers of the present invention can be utilized in various technical fields.

The composite fillers of the present invention can be compounded into various organic resins and rubbers. Examples of such resins and rubbers are organic resins, such as acrylic type resins, styrene type resins, olefin type resins, polyamide resins, polyester resins, phenol resins, unsaturated polyester resins and the like, and; rubbers, such as styrene-butadiene rubbers, polybutadiene rubbers and ethylene-propylene-terpolymers. In the case where the composite fillers of the present invention are compounded into the organic resins and rubbers, the reinforcing effect of the composite filler can be maximized when the composite fillers are compounded in such a manner that the reactivity of the composite fillers is effectively utilized. That is to say, in the case where the composite fillers are compounded into thermosetting resins, the composite fillers should be compounded prior to the curing from the reinforcing point of view. In the case where the composite fillers are compounded into rubbers, the composite fillers should also be compounded prior to the vulcanization from the reinforcing point of view.

In accordance with the preferred embodiment of the present invention, the above-mentioned composite fillers of the present invention can be utilized for the preparation of dental compositions. These dental compositions are prepared by polymerizing vinyl compounds in the presence of the above-mentioned composite fillers.

The vinyl compounds employed in the preparation of the dental compositions of the present inventions include those which can be used, as starting materials, for the manufacture of vinyl type resins, such as acrylic type resins, styrene type resins and the like. Examples of such vinyl monomers are 4-metacryloxyethyl trimellitic acid and its anhydride, bisphenol type epoxy acrylates and their oligomers, urethane dimethacrylates, methyl acrylate, methyl methacrylate, ethyl methacrylate, butyl methacrylate, polyethyleneglycol dimethacrylates, 2,2-bis(p-2'-hydroxy-3'-methacryloxy propoxyphenyl) propane, 2,2-bis(4-methacryloxy polyethoxy phenyl) propane, acrylonitril, vinyl acetate, 2-cyano acrylic acid esters, styrene and divinyl benzene. These vinyl monomers can be employed alone or in any mixture thereof. Among the above-mentioned vinyl monomers, methyl methacrylate, 4-methacryloxyethyl trimellitic acid anhydride, urethane dimethacrylate, bisphenol A type epoxy diacrylate, triethylene glycol dimethacrylate and 2,2-bis(4-methacryloxy polyethoxy phenyl) propane can be preferably employed.

The dental compositions of the present invention can be prepared by polymerizing the vinyl compounds in the presence of the above-mentioned composite fillers by using conventional free-radical initiators, such as, benzoyl peroxide, dicumylperoxide, azobisisobutyronitrile and the like. In order to obtain a large reinforcing effect, the composite fillers are preferably mixed with the vinyl compounds prior to the initiation of the polymerization, but the composite fillers may be added to the vinyl compounds after the initiation of the polymerization.

Although there is no critical amount of the composite fillers compounded into the vinyl compounds, the composite fillers are generally compounded into the vinyl compounds in an amount of at least 10 parts by weight, preferably 30 to 300 parts by weight, based on 100 parts by weight of the vinyl compounds. In the case where the amount of the composite fillers is less than 10 parts by weight, based on 100 parts by weight of the vinyl compounds, the stiffness and the hardness are not preferably improved. Contrary to this, in the case where the amount of the composite fillers is too large, uniform mixing cannot be obtained.

The polymerization can be carried out in any known manner. For instance, in the case where the vinyl compounds are polymerized and cured in the presence of the composite fillers at an elevated temperature, the polymerization is carried out, by using 0.1 to through 3% by weight, based on the weight of the vinyl compounds, of a free-radical initiator, such as benzoyl peroxide, dicumyl peroxide, azobisisobutyronitrile and the like, at a temperature of 50° to 150° C., under an ordinary pressure, or under pressure for 5 minutes to 1 hour. On the other hand, in the case where the vinyl compounds are polymerized and cured in the presence of the composite fillers at an ambient temperature, the polymerization is carried out by separately preparing a mixture of the composite fillers with 0.3 to 3% by weight of, for example, benzoyl peroxide, and a mixture of the vinyl compounds with 0.2 to 3% by weight of aromatic amines, such as dimethyl p-toluidine, diethanol p-toluidine, 1,2,3,4-tetrahydroquinoline, dimethylaniline and the like; followed by uniformly mixing these mixtures, whereby the cured products are obtained at an ambient temperature. The curing time can be widely varied by adjusting the amounts of the curing catalysts. Optionally, any conventional curing accelerator, such as o-benzsulfide, p-toluene sulfinate and the like, can be employed in the curing polymerization in an amount of, for example, 0.1 to 2% by weight, based on the weight of the vinyl compounds. Furthermore, mixtures of the composite fillers and the vinyl compounds can be polymerized and cured at an ambient temperature by the addition of, for example, 0.5 to 3% by weight, based on the weight of the vinyl compounds, of partially oxidized tri-n-butyl borane. In addition, in the case where a photosensitizer, such as benzoin methyl ether or benzoyl isopropyl ether, is previously added to the mixtures of the composite fillers and the vinyl compounds in an amount of, for example, 0.5 to 3% by weight based on the weight of the vinyl compounds, the mixtures can be cured at an ambient temperature by the irradiation of ultraviolet light, visible light, electron beam or the like.

The dental compositions of the present invention may optionally contain other conventional additives and usual compounding ingredients. Examples of such additives and ingredients are inorganic powder fillers, such as kaoline, talc, clay, calcium carbonate, silica, alumina, silica-alumina, calcium phosphate, glass and the like; tackifiers, such as ethylene-vinyl acetate copolymers, waxes, polymerization accelerators, polymerzation modifiers, polymerization inhibitors and the like.

In the case where the present dental compositions are used for dental hard resins for crown and bridge, resin teeth, dental resin shells and the like, the composite fillers and bisphenol A type epoxy methacrylates or urethane dimethacrylates are preferably mixed with each other in approximately equal amounts. More preferably, finely divided hydrophobic silica is advantageously added to the mixtures. These mixtures result in dental compositions having a high hardness and a high strength upon polymerization.

In the case where the present dental compositions are used for dental resin cements, self curing resins for filling and the like, it is preferable that (i) mixtures of the composite fillers with peroxide catalysts and (ii) mixtures of bisphenol A type epoxy acrylate resins with methyl methacrylate, in equal weights, and tertiary aromatic amines be separately prepared, and; then, the mixtures (i) and (ii) are thoroughly mixed in a weight ratio of approximately 4:6. Thus, the curing is initiated 4 to 5 minutes after mixing and is completed in approximately 10 minutes. As a result, uniform composition having good hardness and toughness can be obtained. Furthermore, the use of 4-methacryloxyethyl trimellitic acid anhydride, as the vinyl compound, remarkably improves the adhesiveness of the resultant compositions to teeth and metals.

The present invention will now be illustrated by, but is by no means limited to, the following Examples.

EXAMPLE 1

0.1 g of benzoyl peroxide was dissolved in 10 g of trimethylolpropane trimethacrylate. The solution was placed in an agate mortar and, then, finely divided hydrophobic silica (Aerosil R 972, manufactured by Nippon Aerosil Co., Ltd) was gradually added to the solution in small amounts under mixing. The viscosity of the mixture was gradually increased and, at the time when the mixture became so viscous that it had the form of a solid, the mixture was milled on a pair of small rubber rolls. While milling, additional finely divided silica was intermittently added to the mixture. The total additional amount of the silica was 10 g. The paste composition thus obtained was taken out of the rolls and cured under heating in a press at a mold temperature of 110° C., under a pressure of 150 to 200 kg/cm$^2$, for 10 minutes. The cured product was ground in a ball mill. The composite filler which was sieved through a 250 mesh screen (Tyler) was obtained at a yield of 19.3 g.

The trimethacrylate cured product thus obtained was analyzed by using an infrared spectrophotometer. As a result, a double bond absorption band at 1640 cm$^{-1}$ was observed. Thus, it was confirmed that the ethylenically unsaturated groups were present in the cured product. The specific gravity of the composite filler thus obtained was 1.47 and the Brinell surface hardness thereof was 42. The Brinell surface hardness was determined by using a test piece having a size of 3×10×25 mm, after the test piece was loaded with a steel ball having a diameter of 1.5 mmφ, for 30 seconds. The load was 2.5 kg.

EXAMPLE 2

30 g 2,2-bis(p-2'-hydroxy-3'-methacryloxypropoxy phenyl) propane, 70 g of triethyleneglycol dimethacrylate and 20 g of finely divided hydrophobic silica (Aerosil R 972) were mixed to form 120 g of a viscous liquid. To this liquid mixture, 120 g of the composite filler obtained in Example 1 and 1.2 g of benzoyl peroxide were added. The paste composition thus obtained was placed in a mold and cured under heating in an autoclave at a temperature of 120° C., under a pressure of 4 to 5 atm., for 20 minutes. Thus, a test piece was obtained.

The test piece thus obtained had a Brinell surface hardness of 38, a compression strength of 5700 kg/cm$^2$ and a bending strength of 840 kg/cm$^2$. The specific abrasion of the test piece to poly(methyl methacrylate) in a tooth brush type abrasion testor was 0.13. The compression strength was determined by using a Shimazu Autograph in a manner such that a test piece having a size of 3×3×3 mm was compressed at a compression rate of 2 mm/min. The compression strength was represented by the breaking strength in the above-mentioned test. The bending strength was determined by using a test piece having a size of 2×2×25 mm in such a manner that the test piece was bent in a Shimazu Autograph at a bending rate of 2 mm/min. The distance between two supports was 20 mm. The bending strength was represented by the breaking strength in the above test. The specific abrasion was determined in a tooth brush type abrasion testor in such a manner that a test piece having a size of 10×10×1.5 mm was repeatedly rubbed with a tooth brush made of nylon 5000 times under a load of 500 g. The depths of abrasion of the test pieces of the cured product obtained above and the standard poly (methyl methacrylate) were measured, and the specific abrasion was represented by the ratio of the abrasion depth of the cured product to that of the standard poly(methyl methacrylate).

The cured product of this Example was suitable for use as the dental hard resin for crown and bridge and a resin tooth.

COMPARATIVE EXAMPLE 1

Example 2 was repeated, except that 60 g of finely divided hydrophobic silica (Aerosil R 972) was used in lieu of 120 g of the composite filler obtained in Example 1.

The cured product had a Brinell surface hardness of 32, a compression strength of 4300 kg/cm$^2$, a bending strength of 680 kg/cm$^2$ and a specific abrasion of 0.17.

EXAMPLE 3

0.1 g of benzoyl peroxide was dissolved in 10 g of trimethylolpropane trimethacrylate. The solution was placed in an agate mortar and, then, finely divided hydrophobic silica (Aerosil R 972) was gradually added to the solution in small amounts under mixing. The viscosity of the mixture was gradually increased and, at the time when the mixture became so viscous that it had the form of a solid, the mixture was milled on a pair of small rubber rolls. While milling, additional finely divided silica was intermittently added to the mixture. The total additional amount of the silica was 8 g.

The paste composition thus obtained was taken out of the rolls and cured under heating in a press at a mold temperature of 110° C., under a pressure of 150 to 200 kg/cm$^2$, for 10 minutes. The cured product was ground in a ball mill. The composite filler was sieved through a 250 mesh screen at a yield of 17.1 g.

By infrared analysis of the cured trimethacrylate product by using an infrared spectrophotometer, a double bond absorption band at 1640 cm$^{-1}$ was observed and the remainder of the ethylenically unsaturated groups in the cured product was proved. The specific gravity of the composite filler thus obtained was 1.44 and the Brinell surface hardness thereof was 41.

EXAMPLE 4

Example 2 was repeated, except that 120 g of the composite filler obtained in Example 3 was used in lieu of the composite filler of Example 1.

The cured product had a Brinell surface hardness of 36, a compression strength of 5400 kg/cm$^2$, a bending strength of 790 kg/cm$^2$ and a specific abrasion of 0.14. This cured product was suitable for use as the dental hard resin for crown and bridge and a resin tooth.

EXAMPLE 5

120 g of a viscous liquid was obtained by mixing 50 g of 2,2-bis(4-methacryloxyethoxy phenyl) propane, 50 g of di(methacryloxyethyl) trimethyl hexamethylene diurethane and 20 g of the finely divided hydrophobic silica (Aerosil R 972). To this viscous liquid mixture, 120 g of the composite filler obtained in Example 1 and 1.2 g of benzoyl peroxide were added, and mixed with each other. Thus, a paste composition was obtained.

The paste composition was placed in a mold and cured under heating in an autoclave at a temperature of 120° C., under a pressure of 4 to 5 atom, for 20 minutes. Thus, a test piece was obtained.

The Brinell surface hardness of the test piece was 37, the compression strength thereof was 5400 kg/cm$^2$, the bending strength thereof was 890 and the specific abrasion was 0.14. This cured product was suitable for use as the dental hard resin for crown and bridge and a resin tooth.

EXAMPLE 6

To 120 g of a viscous liquid prepared by mixing 30 g of trimethylolpropane trimethacrylate, 70 g of di(methacryloxyethyl) trimethyl hexamethylene diurethane and 20 g of finely divided hydrophobic silica (Aerosil R 972), 100 g of the composite filler of Example 1 and 1.2 g of benzoyl peroxide was added. A paste composition was obtained upon mixing.

The paste compound thus obtained was placed in a mold and cured under heating in an autoclave at a temperature of 120° C., under a pressure of 4 to 5 atom., for 20 minutes. Thus, a test piece of the cured composition was obtained.

The cured composition thus obtained had a Brinell surface hardness of 35, a compression strength of 5000 kg/cm$^2$, a bending strength of 800 kg/cm$^2$ and a specific abrasion of 0.15. This cured product was suitable for use as the dental hard resin for crown and bridge and are resin tooth.

COMPARATIVE EXAMPLE 2

0.1 g of benzoyl peroxide was dissolved in a mixture of 3 g of 2,2-bis(p-2'-hydroxy-3'-methacryloxypropoxyphenyl) propane and 7 g of triethylene glycol dimethacrylate. This solution was placed in an agate mortar and, then, finely divided hydrophobic silica (Aerosil R 972) was gradually added to the solution in small amounts under mixing. The viscosity of the mixture was gradually increased and, at the time when the mixture became so viscous that it had the form of a solid, the mixture was milled on a pair of small rubber rolls. While milling on the rolls, additional finely divided hydrophobic silica was intermittently added to the mixture. The total additional amount of the silica was 8 g.

The paste composition thus obtained was taken out of the rolls and cured under heating in a press at a mold temperature of 110° C., under a pressure of 150 to 200 kg/cm², for 10 minutes. The cured product was ground in a ball mill. The yield of the composite filler, which was sieved through a 250 mesh screen, was 17.3 g.

The dimethacrylate cured product thus obtained was analyzed by using an infrared spectrophotometer. As a result, a double bond absorption band at 1640 cm$^{-1}$ was slightly observed, which means that only slight amounts of the ethylenically unsaturated bonds remained. The specific gravity of the composite filler was 1.42 and the Brinell surface hardness thereof was 39.

COMPARATIVE EXAMPLE 3

Example 1 was repeated, except that the composite filler prepared in Comparative Example 2 was used in lieu of the composite filler of Example 1.

The cured product obtained had a Brinell surface hardness of 30.1, a compression strength of 4200 kg/cm², a bending strength of 710 kg/cm² and a specific abrasion of 0.18.

EXAMPLE 7

A liquid mixture of 50 g of epoxy acrylate resin (Ripoxy VR-90, manufactured by Showa Kobunshi Co.), 50 g of methylmethacrylate and 0.5 g of dimethyl-p-toluidine, and a powder mixture of 100 g of the composite filler of Example 1 and 1 g of benzoyl peroxide were mixed in a weight ratio of 3:2. Thus, a paste composition was prepared.

The paste composition was placed in a mold and cured at ambient temperature for approximately 6 minutes. The cured product was subjected to a film test according to JIS (Japanese Industrial Standard)-T-6602. The film thickness was 15 microns, the degradation percentage was zero and the crushing resistance was 1010 kg/cm². This composition was suitable for use as dental resin cement.

EXAMPLE 8

A liquid mixture of 50 g of the epoxy acrylate resin used in Example 7, 50 g of methyl methacrylate, 50 g of 4-methacryloxy ethyl trimellitic acid anhydride and 0.2 g of diethanol-p-toluidine, and a powder mixture of 100 g of the composite filler of Example 1 and 1 g of benzoyl peroxide and 0.5 g of p-toluene sulfinic acid sodium salt were mixed in an weight ratio of 3:2. Thus, a paste composition was obtained. The paste composition thus obtained was placed in a mold and cured at ambient temperature for six and a half minutes.

The paste composition was subjected to a film test according to JIS-T-6602. The thickness of the film was 17 microns, the degradation percentage was zero and the crushing resistance was 980 kg/cm².

Furthermore, the paste composition was coated on a test piece, to which an acryl resin rod was bonded, and cured at an ambient temperature. The adhesiveness of the composition to the acryl resin rod was determined as follows.

The acryl resin rod coated with the paste composition was dipped in water at 37° C. for 24 hours. The rod was taken out of the water and was subjected to a tensile test by using s Shimazu Autograph Type DSS-500 at a test speed of 2 mm/min. Furthermore, the acryl resin rod coated with the paste composition was first dipped in water at 37° C. for 24 hours and, then, the rod was alternately and repeatedly dipped in water at 4° C. and at 60° C. for 1 minute each. This repeating cycle was conducted 60 times (the total of the dipping times was 2 hours). The results are as follows.

TABLE

| Tensile Adhesive Strength | 24 Hours in Water (kg/cm²) | 60 Times Cycle (kg/cm²) |
|---|---|---|
| Ivory Square Rod Ground by Emery Paper | 30 | — |
| Bovine Enamel Etched by 65% Phosphoric acid*¹ | — | 115 |
| Ni—Cr Alloy Ground by Emery Paper | 218 | — |
| Au—Pd Alloy Ground by Emery Paper | 129 | — |
| Surface Treated*² Au—Pd Alloy | — | 108 |

*¹30 second treatment
*²After 800° C. heat treatment for 1 hour, sample was subjected to acid washing, followed by heat treatment at 600° C. for 30 min.

The paste composition of this Example was suitable for use as a dental resin cement.

EXAMPLE 9

A liquid mixture of 60 g of triethylene glycol dimethacrylate, 40 g of the epoxy acrylate resin used in Example 7 and 0.4 g of dimethyl-p-toluidine, and the powder mixture used in Example 7 were mixed in a weight ratio of 3:2. Thus, a paste composition was obtained.

The paste composition was placed in a mold and cured at an ambient temperature for approximately 6 minutes. The paste composition was subjected to a film test according to JIS-T-6602. The film thickness was 18 microns, the degradation percentage was zero and the crushing resistance was 1080 kg/cm².

This paste composition was suitable for use as a resin cement and an self curing resin for filing.

We claim:
1. A composite filler obtained by:
   (1) precuring the acrylate or methacrylate of a polyhydric alcohol having at least three ethylenically unsaturated groups in the molecule thereof at a temperature from 40° to 250° C. under a pressure of from 10 to 300 kg/cm²G by using a free-radical initiator in the presence of silica as an inorganic filler such that a portion of the ethylenically unsaturated groups in the acrylate or methacrylate remains; and thereafter
   (2) grinding the resultant prepolymer into a powder.
2. A composite filler as claimed in claim 1, wherein said polyhydric alcohol is selected from the group consisting of glycerine, trimethylol ethane, trimethylol propane and pentaerythritol.
3. A composite filler as claimed in claim 2, wherein said acrylate or methacrylate is triacrylate or trimethacrylate of trimethylol propane.
4. A composite filler as claimed in claim 1, wherein said free-radical initiator is benzoyl peroxide, dicumyl peroxide or azobisisobutyronitrile.
5. A composite filler as claimed in claim 1, wherein the weight ratio of the acrylate or methacrylate to the silica is within the range of from 20:80 to 80:20.

* * * * *